United States Patent
Stanjek et al.

(10) Patent No.: US 8,158,818 B2
(45) Date of Patent: Apr. 17, 2012

(54) PROCESS FOR PREPARING ISOCYANATOORGANOSILANES

(75) Inventors: Volker Stanjek, Ampfing (DE); Frank Baumann, Tittmoning (DE); Thomas Frey, Burghausen (DE)

(73) Assignee: Wacker Chemie AG, Munich (DE)

( * ) Notice: Subject to any disclaimer, the term of this patent is extended or adjusted under 35 U.S.C. 154(b) by 348 days.

(21) Appl. No.: 12/516,842

(22) PCT Filed: Nov. 28, 2007

(86) PCT No.: PCT/EP2007/062935
§ 371 (c)(1),
(2), (4) Date: May 29, 2009

(87) PCT Pub. No.: WO2008/068175
PCT Pub. Date: Jun. 12, 2008

(65) Prior Publication Data
US 2010/0069656 A1 Mar. 18, 2010

(30) Foreign Application Priority Data

Dec. 4, 2006 (DE) .......................... 10 2006 057 118

(51) Int. Cl.
*C07C 263/00* (2006.01)
(52) U.S. Cl. ..................................................... 560/345
(58) Field of Classification Search .................. None
See application file for complete search history.

(56) References Cited

U.S. PATENT DOCUMENTS

| | | | | |
|---|---|---|---|---|
| 3,607,901 A | * | 9/1971 | Berger | 556/414 |
| 5,393,910 A | * | 2/1995 | Mui et al. | 556/414 |
| 6,008,396 A | | 12/1999 | Sheridan et al. | |
| 6,388,117 B2 | | 5/2002 | Pinske | |
| 7,060,849 B1 | | 6/2006 | Childress et al. | |
| 2002/0016486 A1 | * | 2/2002 | Pinske | 556/411 |
| 2004/0049064 A1 | | 3/2004 | Kammel et al. | |
| 2004/0204539 A1 | | 10/2004 | Schindler et al. | |
| 2007/0066784 A1 | | 3/2007 | Radinger et al. | |
| 2007/0149797 A1 | | 6/2007 | Rudinger et al. | |

FOREIGN PATENT DOCUMENTS

| | | |
|---|---|---|
| DE | 10108543 C1 | 4/2002 |
| EP | 0649850 A1 | 4/1995 |
| EP | 1010704 A2 | 6/2000 |
| EP | 1343793 B1 | 5/2004 |
| EP | 1421129 B1 | 6/2005 |
| WO | 2005055974 A2 | 6/2005 |
| WO | 2005056564 A1 | 6/2005 |

OTHER PUBLICATIONS

"Evaporation" in Ullmann's Encyclopedia of Industrial Chemistry, Published Online: Jun. 15, 2000, Copyright © 2002 by Wiley-VCH Verlag GmbH & Co. KGaA, pp. 1-36.*

* cited by examiner

*Primary Examiner* — Karl J Puttlitz
(74) *Attorney, Agent, or Firm* — Brooks Kushman P.C.

(57) ABSTRACT

Isocyanate-functional silanes, particularly isocyanate-functional α-silanes, are prepared in good yield by a liquid phase thermolysis conducted in the presence of a catalyst at a pressure of >100 mbar, or >80 mbar when a thin-film evaporator is used.

22 Claims, No Drawings

PROCESS FOR PREPARING ISOCYANATOORGANOSILANES

CROSS-REFERENCE TO RELATED APPLICATION

This application is the U.S. national phase of PCT Appln. No. PCT/EP2007/062935 filed Nov. 28, 2007 which claims priority to German application DE 10 2006 057 118.5 filed Dec. 4, 2006.

BACKGROUND OF THE INVENTION

1. Field of the Invention

The invention relates to a process for preparing isocyanatoalkylsilanes.

2. Description of the Related Art

For a considerable time there has been great interest in an economic method of preparing isocyanatoorganosilanes in high yields and purities. The stated compounds are of high economic importance.

Isocyanatosilanes can be used, for example, as adhesion promoters between organic polymers and inorganic materials. In particular, however, isocyanatoorganosilanes are used in industry for terminating organic polyols, e.g., polyether polyols, polyurethanes, polyesters or poly(meth)acrylates. The resulting alkoxysilane-terminated prepolymers cure on contact with atmospheric moisture and are used, among other things, as adhesives and sealants or else as film-forming resins or constituents thereof.

In the prior art in these contexts it is mostly conventional γ-isocyanatopropylsilanes of the general formula (1) that are used

$$OCN—(CH_2)_3—SiR'_y(OR'')_{3-y} \quad (1),$$

where R' and R" are alkyl radicals and y is a number of 0-3, preferably 3 or 2.

More recently, however, particular interest has focused on the so-called α-isocyanatomethylsilanes of the general formula (2)

$$OCN—(CH_2)—SiR'_y(OR'')_{3-y} \quad (2),$$

where R' and R" and y have the definitions stated above.

These α-isocyanatomethylsilanes feature particularly high reactivity to atmospheric moisture and are suitable for preparing alkoxysilane-terminated prepolymers with a high but regulable curing rate (described, for example, in EP 1 421 129). Moreover, the corresponding α-silane-terminated prepolymers can be crosslinked even without the tin catalysts which are controversial from the standpoint of toxicology (described inter alia in EP 1 421 129).

There are various known processes for preparing isocyanatoorganosilanes. EP 1 010 704, for instance, describes a process for preparing γ-isocyanatoorganosilanes that cleaves carbamatoorganosilanes in a combined cleaving and rectifying column at pressures of preferably 40-80 mbar to form the corresponding isocyanatoorganosilanes. That process adds tin-II chloride catalyst to the liquid phase. A disadvantage of that process is its very low conversion rates, which necessitate, moreover, a high level of cost and apparatus complexity in order to isolate and purify the reaction products. To date, therefore, this process has not been employed industrially.

DE 101 08 543 describes the preparation of isocyanatoorganosilanes from the corresponding carbamatoorganosilanes and alkyl- or vinylchlorosilanes. This process as well has proved unsuitable for industrial production and to date has therefore not been employed.

Known from EP 0 649 850 is a process in which carbamatoorganosilanes are cleaved thermally to form isocyanatoorganosilanes and methanol. This cleavage takes place in the gas phase under atmospheric or reduced pressure. The reaction is preferably carried out in a tube reactor, in which the evaporated carbamatosilane is heated to temperatures which lie well above the evaporation temperature of this silane. An improvement to this process, in which the carbamate cleavage is carried out in the presence of a heterogeneous catalyst, is known, furthermore, from EP 1 343 793. Disadvantages of these processes include the high thermal load on the highly reactive reaction product, and the high level of equipment and energy expenditure and complexity.

The thermal cleavage of carbamatoorganosilanes to form isocyanatoorganosilanes and methanol is described, moreover, in U.S. Pat. No. 6,008,396. There, carbamatoorganosilanes in inert hot media, with elimination of alcohol, are converted into the corresponding isocyanatosilanes, which are then removed directly from the reaction mixture by distillation. With this process as well, the reaction products are exposed to high thermal loads. Moreover, byproducts and impurities may accumulate in the inert medium.

A further process, in which the isocyanatoorganosilanes are prepared under the action of microwaves, is described in WO 2005/056564. In WO 2005/055974, finally, this microwave process is described in combination with fluidizing particulate solids. This process as well entails a high level of technical complexity and expense.

SUMMARY OF THE INVENTION

An object of the invention, therefore, was to develop a substantially simpler process which can be implemented industrially without problems, and which allows isocyanatoalkylsilanes, especially isocyanatoalkylsilanes of the formulae (1) and (2), to be prepared in high yields.

The invention provides a process for cleaving carbamate-functional silane (C) to isocyanate-functional silane (I) and alcohol, wherein a) the liquid carbamate-functional silane (C) is heated in an evaporating unit under a pressure of more than 100 mbar and under the action of a catalyst (K), and b) the resulting isocyanate-functional silane (I) is evaporated.

The invention further pertains to a process where the evaporating unit comprises a thin film evaporator operating at a pressure of at least 80 mbar, with a film thickness not exceeding 5 cm.

DETAILED DESCRIPTION OF THE PREFERRED EMBODIMENTS

One important aspect of the invention is the implementation of the reaction according to the invention in a liquid film with thin thicknesses, allowing rapid evaporation of the isocyanate functional silane (I) formed and also of the alcohol formed as a second cleavage product. This rapid evaporation first prevents the possibility of an equilibrium becoming established in the catalyst (K)-containing liquid phase and hence the reaction coming to a standstill. At the same time, the removal of the isocyanate functional silane (I) prevents the possibility of it being degraded by subsequent reactions, such as by formation of isocyanurate, for example. The process is preferably conducted in the absence of high boiling inert liquids, preferably employing only carbamate-functional silane, catalyst, recycle streams, and inert gas.

The invention accordingly further provides a process for cleaving carbamate-functional silane (C) to isocyanate-functional silane (I) and alcohol, wherein
a) the liquid carbamate-functional silane (C) is heated in a liquid film (F) having a thickness of not more than 5 cm and under a pressure of at least 80 mbar and under the action of a catalyst (K), and
b) the resulting isocyanate-functional silane (I) is evaporated.

The preferred thickness of the liquid film (F) in this case is preferably not more than 2 cm, more preferably not more than 1 cm, with particular advantage being possessed by film thicknesses of not more than 0.5 cm or even of not more than 0.3 cm.

Typically the alcohol which is formed at the same time is not substantially heavier or more readily volatile than the isocyanate-functional silane (I), and in that case is evaporated together with the latter.

It is possible, although not desired, to evaporate some of the carbamate-functional silane (C) used as well.

Thereafter the evaporated reaction product is preferably subjected directly to fractional condensation, in which case any alcohol present is separated off preferably in gas form, and the isocyanate-functional silane (I) and the carbamate-functional silane (C), where present, are condensed together or else, where appropriate, separately in succession. The removal of the alcohol prevents back-reaction of the isocyanate-functional silane (I) formed. The alcohol is removed preferably in a condenser or in a simple separating column, in which the alcohol is taken off in gas form, and silanes (I) and (C) are jointly removed by condensation.

The evaporating unit is preferably a thin-film, falling-film or short-path evaporator. With particular preference the inventive cleaving of the carbamate-functional silanes (C) is carried out in a conventional thin-film evaporator. This evaporator is preferably operated with a wall temperature >180° C., more preferably >220° C., and most preferably with wall temperatures of >260° C. It is preferred for more than 10% and more preferred for more than 20% of the material introduced into the thin-film evaporator to be evaporated. In one particular embodiment of the invention, significantly higher evaporation rates are achieved, of more than 30%, or even more than 50%. The material evaporated preferably constitutes a mixture of undecomposed carbamate-functional silane (C), isocyanate-functional silane (I), and alcohol. With preference at least 35 percent by weight, more preferably at least 50 percent by weight, of the evaporated material is composed of the respective isocyanate-functional silane (I).

In the process of the invention the evaporation is carried out preferably at pressures >100 mbar, with particular preference being given to pressures >200 mbar or >500 mbar. In order to maximize the evaporation temperature and hence the conversion rates, however, the evaporation is preferably carried out entirely without vacuum—that is, at atmospheric pressure —or even with a slight overpressure, particular preference being given to a pressure range of 1-2 bar. In a further embodiment of the invention the evaporation is carried out preferably at pressures >2 bar or even at pressures >3 bar.

In one preferred embodiment of the invention an inert gas stream, composed of argon, hydrogen or nitrogen, for example, is passed through this evaporating unit during the evaporating operation. This gas stream is preferably heated to temperatures >200° C., more preferably to temperatures >300° C. or even to temperatures >400° C., before being introduced into the evaporating unit. This heated stream of carrier gas supports the heating and evaporation of the reaction mixture. Nitrogen is a preferred gas.

The gas stream and liquid stream can be guided in the evaporating unit in the same direction or else in opposite directions, i.e., in cocurrent or countercurrent flow. In one preferred embodiment, however, a countercurrent regime is preferred.

In one preferred embodiment of the invention the carbamate-functional silane (C) is preheated before being introduced into the evaporating unit. In that case it is preferably heated to temperatures >100° C., more preferably to temperatures >120° C. and in particular to temperatures >130° C. This preheating accelerates the further heating of the reaction mixture in the evaporating unit to the maximum reaction and evaporation temperature.

The catalyst (K) may be a catalyst embedded in a fixed bed in the evaporating unit, the fixed bed being located, for example, on the wall of the thin-film evaporator. The catalyst is preferably one which is admixed with the carbamate-functional silane (C). With particular preference the catalyst (K) is liquid or else soluble in the carbamate-functional silane (C). In other words, the catalysis involved is preferably homogeneous. Preferred catalysts (K) in this context are all of the compounds which—particularly in PU chemistry—are also used to catalyze condensation reactions of isocyanates and alcohols. Here it is possible, by way of example, to identify the organotin compounds that are typically used, such as dibutyltin dilaurate, dioctyltin dilaurate, dibutyltin diacetylacetonate, dibutyltin diacetate or dibutyltin dioctoate, etc. It is also possible to use divalent tin catalysts such as tin diacetate or tin dilaurate. Furthermore, it is also possible to employ bismuth catalysts, e.g., the Borchi catalyst, titanates, e.g., titanium(IV) isopropoxide, iron(III) compounds, e.g., iron(III) acetylacetonate, or else amines, examples being triethylamine, tributylamine, 1,4-diazabicyclo[2.2.2]octane, 1,8-diazabicyclo[5.4.0]undec-7-ene, 1,5-diazabicyclo[4.3.0]non-5-ene, N,N-bis(N,N-dimethyl-2-aminoethyl)methylamine, N,N-dimethylcyclohexylamine, N,N-dimethylphenylamine, N-ethylmorpholinine, etc. Organic or inorganic Brönsted acids as well, such as acetic acid, trifluoroacetic acid or benzoyl chloride, hydrochloric acid, phosphoric acid, its monoesters and/or diesters, such as butyl phosphate, (iso)propyl phosphate, dibutyl phosphate, etc., are suitable as catalysts (K). It is of course also possible to use combinations of two or more catalysts. It is preferred to use catalysts which are nonvolatile or whose volatility is low, especially the aforementioned metal complexes, with particular preference being given to tin(IV), tin(II) and iron(III) complexes. This catalyst (K) is used preferably at concentrations of 1-10,000 ppm, with particular preference being given to concentrations of 10-5000 ppm or 100 -2000 ppm.

In one preferred embodiment of the invention the bottom product from the thin-film evaporator, comprising catalyst (K) and carbamate-functional silane (C), is mixed with fresh carbamate-functional silane (C) and used again in the process of the invention. Before this recycle, if appropriate, parts of the bottom product may be removed from the process in order to prevent accumulation of byproducts and/or impurities. It is also possible to add fresh catalyst (K). In this way, the catalyst (K) is recycled completely or else at least to a large extent. Of course it is also possible for catalytically active degradation products or rearrangement products, formed from the originally added catalyst (K) during preceding passages of the thin-film evaporator, to serve as catalyst (K).

In the process of the invention it is preferred for isocyanate-functional silane (I) of the general formula (3)

$$OCN-(CH_2)_x-SiR^1_a(OR^2)_{3-a} \qquad (3),$$

to be prepared starting from carbamate-functional silane (C) of the general formula (4)

$$R^3O-CO-HN-(CH_2)_x-SiR^1_a(OR^2)_{3-a} \quad (4),$$

where
R$^1$ is an optionally halogen-substituted alkyl, cycloalkyl, alkenyl or aryl radical having 1-10 carbon atoms,
R$^2$ is an acyl, alkyl, alkenyl, cycloalkyl or aryl radical having 1-10 carbon atoms or an ω-oxaalkyl-alkyl radical having a total of 2-10 carbon atoms,
R$^3$ is an alkyl radical having 1-6 carbon atoms or an ω-oxaalkyl-alkyl radical having a total of 2-10 carbon atoms,
x is 1-8, and
a is 0, 1, 2 or 3.

Preferred radicals R$^1$ are methyl, ethyl or phenyl groups. The radicals R$^2$ and R$^3$ are preferably acetyl and more preferably methyl groups or ethyl groups. Preferably the radicals R$^2$ and R$^3$ are identical. a is preferably 0, 1 or 2, more preferably 0 or 1. The variable x is preferably 1 or 3, particular preference being given to a value of 1—i.e., the preparation of α-isocyanatomethylsilanes.

Especially for the preparation of α-isocyanatomethylsilanes (I) the process of the invention is of surprisingly high suitability. By virtue of a higher cleavage temperature of the corresponding carbamatosilanes (C), these silanes (I) are comparatively poorly preparable by the prior-art processes.

The purification of the isocyanate-functional silanes (I) prepared in accordance with the invention is preferably accomplished by means of one or more distillation steps. In the course of their purification, the isocyanate-functional silanes (I) are preferably handled exclusively under inert gas, in order to maximize the storage stability of these silanes. This inert gas atmosphere preferably has a water content below 1000 ppm, particular preference being given to a water content below 250 ppm. The inert gas used is preferably dried air, nitrogen or noble gases, particular preference being given to nitrogen.

EXAMPLES

Example 1

α-Carbamatomethyldimethoxymethylsilane (GENIOSIL® XL 65 from Wacker Chemie AG) is admixed with 0.5% by weight of dibutyltin dilaurate. The resulting mixture is preheated in an inductively heated tube to about 130° C.
employing about 2.2 KW and introduced into a thin film evaporator with the following technical data
evaporator surface area: 0.25 m$^2$
electrical coil heating with about 6 KW, evaporation taking place under the following conditions:
pressure: 1.1 bar (absolute)
wall temperature of the thin-film evaporator: 275° C.
distillate/bottom product ratio: 26 kg/6 kg Subsequently the vapor is passed into a suitable condenser, in which a silane mixture consisting of carbamatosilane and isocyanatosilane is condensed out, while the methanol formed is separated off as a gas. The result is a silane mixture containing about 83 mol % α-isocyanatomethyldimethoxymethylsilane and 17 mol % α-carbamatomethyldimethoxymethylsilane.

The bottom product of the thin-film evaporator is composed of pure α-carbamatomethyldimethoxymethylsilane. Byproducts or degradation products are formed in amounts <<5% by weight.

Comparative Example 2

Pure α-carbamatomethyldimethoxymethylsilane is evaporated in the thin-film evaporator described in example 1, without addition of catalyst. Owing to the absence of a chemical reaction, the evaporating conditions have to be varied somewhat:
pressure: 1.1 bar (absolute)
wall temperature of the thin-film evaporator: 320° C. to 340° C.
distillate/bottom product ratio: 26 kg/6 kg The vapor phase is worked up as described in example 1. The result is a silane mixture which contains about 16 mol % α-isocyanatomethyldimethoxymethylsilane and 84 mol % α-carbamatomethyldimethoxymethylsilane.

Comparative Example 3

α-Carbamatomethyldimethoxymethylsilane (GENIOSIL® XL 65 from Wacker) is admixed with 0.5% by weight of dibutyltin dilaurate and evaporated in vacuo in the thin-film evaporator described in example 1. Owing to the absence of a chemical reaction, the evaporating conditions have to be varied somewhat:
pressure: 5 mbar
wall temperature of the thin-film evaporator: 220° C.
distillate/bottom product ratio: 50/50

The vapor phase is worked up as described in example 1. The result is a silane mixture which contains about 3 mol % α-isocyanatomethyldimethoxymethylsilane and 97 mol % α-carbamatomethyldimethoxymethylsilane.

The invention claimed is:

1. A process for cleaving a carbamate-functional silane (C) to isocyanate functional silane (I) and alcohol, comprising
heating the liquid carbamate-functional silane (C) in an evaporating unit under a pressure of greater than 100 mbar in the presence of a catalyst (K), and
evaporating the resulting isocyanate-functional silane (I), wherein when the evaporating unit is a thin-film evaporator, the liquid carbamate-functional silane (C) is heated in a liquid film (F) having a thickness of not more than about 5 cm.

2. The process of claim 1, wherein the evaporating unit is a falling-film or short-path evaporator.

3. The process of claim 1, wherein the carbamate-functional silane (C) is preheated to a temperature >100° C. before being introduced into the evaporating unit.

4. The process of claim 1, wherein the catalyst (K) is liquid or is soluble in the carbamate functional silane (C).

5. The process of claim 3, wherein the catalyst (K) is liquid or is soluble in the carbamate functional silane (C).

6. The process of claim 1, wherein an isocyanate-functional silane (I) of the formula (3)

$$OCN-(CH_2)_x-SiR^1_a(OR^2)_{3-a} \quad (3),$$

is prepared from a carbamate-functional silane (C) of the formula (4)

$$R^3O-CO-HN-(CH_2)_x-SiR^1_a(OR^2)_{3-a} \quad (4),$$

where
R$^1$ is an optionally halogen substituted alkyl, cycloalkyl, alkenyl or aryl radical having 1-10 carbon atoms,
R$^2$ is an acyl, alkyl, alkenyl, cycloalkyl or aryl radical having 1-10 carbon atoms or an ω-oxaalkyl-alkyl radical having a total of 2-10 carbon atoms,
R$^3$ is an alkyl radical having 1-6 carbon atoms or an ω-oxaalkyl-alkyl radical having a total of 2-10 carbon atoms,
x is 1-8, and
a is 0, 1, 2 or 3.

7. The process of claim 6, wherein x is 1 or 3.

8. The process of claim 1, wherein the thickness of the liquid film (F) is not more than 1 cm.

9. The process of claim 1, wherein a thin-film evaporator is employed, and reaction is conducted at a pressure greater than 1 bar.

10. The process of claim 9, wherein the pressure is greater than 2 bar.

11. The process of claim 1, wherein a thin-film evaporator with a wall temperature greater than 180° C. is employed.

12. The process of claim 1, wherein a crude product stream comprising isocyanate-functional silane and alcohol is removed from the reactor and fed to a separation apparatus, alcohol being removed as a gas stream from the crude product stream.

13. The process of claim 12, wherein the crude product stream further comprises carbonate-functional silane, and the carbonate-functional silane is separated from the isocyanate-functional silane and recycled back to the evaporator unit.

14. The process of claim 13, wherein the crude product stream further comprises byproducts, and these byproducts are at least partially removed from the carbonate-functional silane prior to its recycle to the evaporator unit.

15. The process of claim 1, wherein an inert gas, heated to a temperature of about 200° C. or greater is introduced into the evaporator unit.

16. The process of claim 1, wherein the pressure is greater than 500 mbar.

17. The process of claim 1, wherein the pressure from 1 to 2 bar.

18. The process of claim 1, wherein greater than 30 weight percent of material introduced into the evaporating unit is evaporated.

19. The process of claim 1, wherein greater than 50 weight percent of material introduced into the evaporating unit is evaporated.

20. The process of claim 2, wherein the carbamate-functional silane (C) is preheated to a temperature >100° C. before being introduced into the evaporating unit.

21. The process of claim 2, wherein the catalyst (K) is liquid or is soluble in the carbamate functional silane (C).

22. The process of claim 20, wherein the catalyst (K) is liquid or is soluble in the carbamate functional silane (C).

* * * * *